US009079011B2

(12) United States Patent
Zastrow et al.

(10) Patent No.: US 9,079,011 B2
(45) Date of Patent: Jul. 14, 2015

(54) MICROWAVE HYPERTHERMIA TREATMENT SYSTEM

(75) Inventors: Earl Zastrow, Madison, WI (US); Susan Hagness, Madison, WI (US); Barry Van Veen, McFarland, WI (US); Joshua Medow, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1229 days.

(21) Appl. No.: 12/983,535

(22) Filed: Jan. 3, 2011

(65) Prior Publication Data
US 2012/0172954 A1 Jul. 5, 2012

(51) Int. Cl.
A61N 5/01 (2006.01)
A61N 5/02 (2006.01)
A61B 19/00 (2006.01)

(52) U.S. Cl.
CPC ............. *A61N 5/025* (2013.01); *A61B 19/50* (2013.01); *A61B 2019/501* (2013.01); *A61N 2005/027* (2013.01)

(58) Field of Classification Search
CPC ................ A61B 18/1815; A61B 2019/501; A61B 2019/505
See application file for complete search history.

(56) References Cited

U.S. PATENT DOCUMENTS

| 4,860,752 | A | * | 8/1989 | Turner | 607/102 |
| 5,251,645 | A | | 10/1993 | Fenn | |
| 5,441,532 | A | | 8/1995 | Fenn | |
| 5,810,888 | A | * | 9/1998 | Fenn | 607/154 |
| 6,618,620 | B1 | * | 9/2003 | Freundlich et al. | 607/27 |
| 8,556,888 | B2 | * | 10/2013 | Nields et al. | 606/27 |
| 2003/0055471 | A1 | * | 3/2003 | Fenn et al. | 607/101 |
| 2003/0069619 | A1 | * | 4/2003 | Fenn et al. | 607/101 |
| 2005/0192764 | A1 | * | 9/2005 | Holland | 702/28 |
| 2007/0208399 | A1 | * | 9/2007 | Turner et al. | 607/100 |
| 2008/0116891 | A1 | * | 5/2008 | van der Kouwe et al. | 324/312 |
| 2008/0183251 | A1 | | 7/2008 | Azar et al. | |
| 2009/0221999 | A1 | * | 9/2009 | Shahidi | 606/33 |
| 2009/0326420 | A1 | * | 12/2009 | Moonen et al. | 601/3 |
| 2010/0010596 | A1 | | 1/2010 | Persson et al. | |
| 2010/0063496 | A1 | * | 3/2010 | Trovato et al. | 606/34 |
| 2010/0081971 | A1 | * | 4/2010 | Allison | 601/2 |
| 2010/0222698 | A1 | | 9/2010 | Turnquist et al. | |
| 2011/0015628 | A1 | * | 1/2011 | Dalal et al. | 606/34 |
| 2011/0245900 | A1 | * | 10/2011 | Turner et al. | 607/100 |
| 2011/0251607 | A1 | * | 10/2011 | Kruecker et al. | 606/34 |
| 2013/0158440 | A1 | * | 6/2013 | Allison | 601/2 |

FOREIGN PATENT DOCUMENTS

| WO | 0180708 | 11/2001 |
| WO | 2008151469 | 12/2008 |
| WO | 2010047818 | 4/2010 |

* cited by examiner

Primary Examiner — Kaitlyn Smith
(74) Attorney, Agent, or Firm — Boyle Fredrickson, S.C.

(57) ABSTRACT

A microwave hyperthermia treatment system employs a set of antennas individually controllable to provide different phase and amplitude outputs and controlled to cycle through different sets of phases and amplitudes over time to minimize the effect of hotspots formed by any given set of phases and amplitudes and creating limiting high temperatures outside of a desired treatment area.

7 Claims, 4 Drawing Sheets

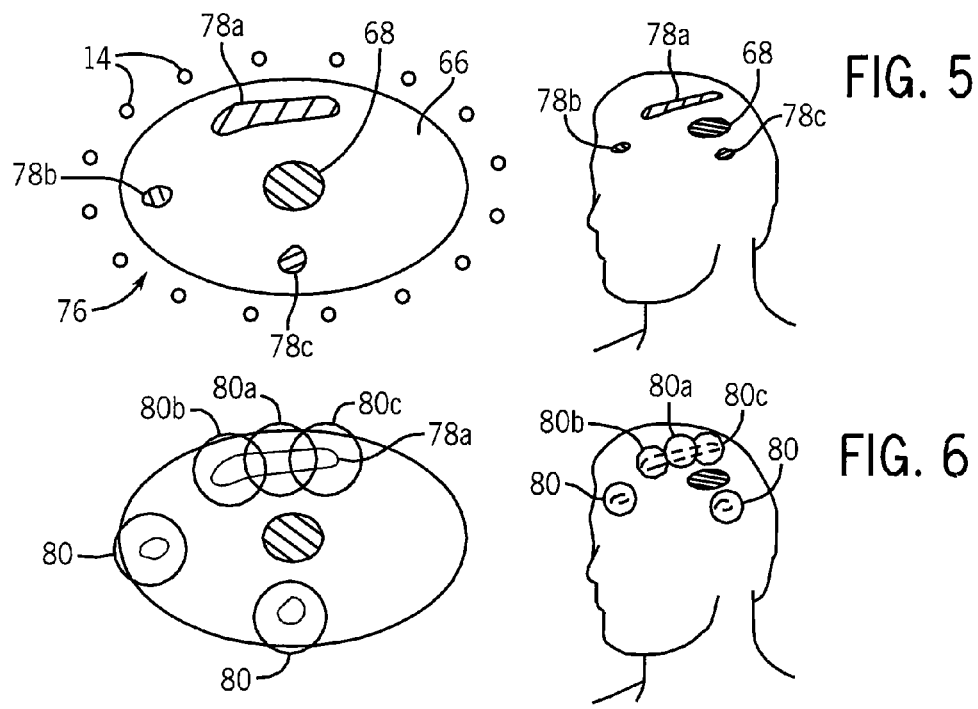
FIG. 5
FIG. 6
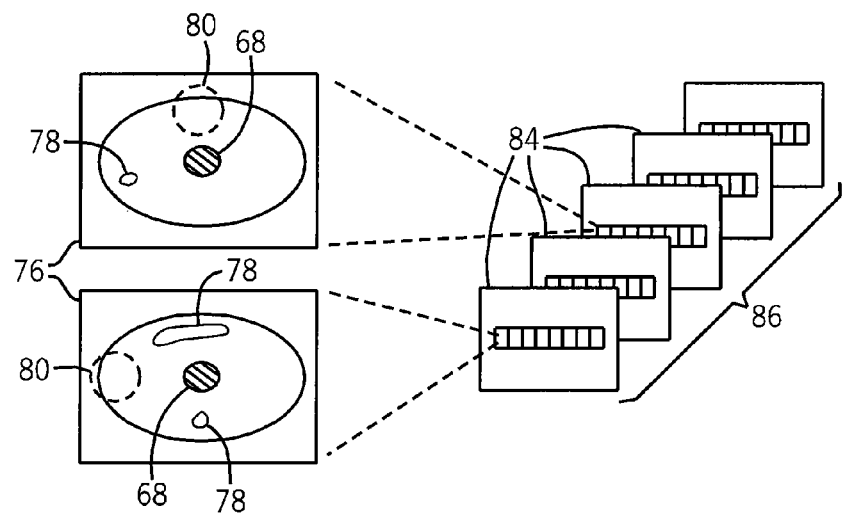
FIG. 7

MICROWAVE HYPERTHERMIA TREATMENT SYSTEM

STATEMENT REGARDING FEDERALLY-SPONSORED RESEARCH OR DEVELOPMENT

This invention was made with government support under 0625054 awarded by the National Science Foundation. The government has certain rights in the invention.

CROSS REFERENCE TO RELATED APPLICATIONS

Background of the Invention

The present invention relates to medical hyperthermia treatment systems and in particular to an improved method for controlling microwave antennas for selective heating of tissue.

Hyperthermia treatment elevates the temperature of tissues for a variety of purposes including: (i) destroying tissues such as tumors by the application of heat, (ii) increasing the susceptibility of heated tissue to chemical or radiation therapy, and (iii) triggering heat activated or released drugs. It is generally known to use microwave electromagnetic radiation for hyperthermia treatment. Microwaves provide a number of advantages including an ability to pass though some body structures such as the skull for treatment of the brain, and an ability to be focused to permit, for example, localized treatment of a tumor surrounded by tissue with reduced damage to the surrounding tissue.

Microwave energy may be focused, for example, through a phased array of the antennas. In this technique, the phase and amplitude of the microwave radiation supplied to each antenna is adjusted to create constructive interference at the tumor site among radiated waves from each antenna and destructive interference outside of the tumor site among the waves from each antenna. By proper phasing of the emitted microwaves, the power deposited on the tumor may be increased over that deposited outside of the tumor region. The determination of the proper phase and amplitude of the microwave power at each antenna may take into account the electrical properties of the intervening tissue of the patient to correct for phase shifts and attenuation caused by this tissue.

As a practical matter, it is impossible to find a given set of phase and amplitude values that focus microwave radiation for an arbitrary treatment pattern while completely suppressing the deposition of microwave energy outside of the treatment pattern. Unwanted heated zones outside of the tumor region inevitably form to limit the amount of energy that can be applied to the tumor without damage to healthy tissue. Sometimes tissue in the hot zones can be cooled, for example, by chilled water or air applied to the skin.

SUMMARY OF THE INVENTION

The present inventors have recognized that the unwanted heated zones can be minimized by cycling through different antenna array settings each having a common treatment zone but providing relative "cold spots" or suppression regions in different locations. Effective hyperthermia treatment schedules can be produced by offsetting potential hotspots in a given location in one antenna array setting with cold spots in that location in a different antenna array setting.

In one embodiment, the invention provides a treatment planning system including an electronic computer executing a stored program to receive data characterizing tissue in a tissue region of a patient and data defining a treatment region being a portion of the tissue region. The planning system may use the data characterizing the tissue to model a set of power deposition patterns and associated temperature distribution profiles from a known array of antennas emitting different given amplitudes and phases of radiofrequency power for each power deposition pattern. A treatment schedule may then be generated by selecting among this set of power deposition patterns, each having different hotspots and suppression regions of relative elevated and low temperatures, respectively, so that suppression regions of some selected power deposition patterns are matched to the potential hotspots of other power deposition patterns to control average power deposition to the tissue region outside the treatment region.

It is thus a feature of at least one embodiment of the invention to reduce hotspots that are created in focusing the signals transmitted by an antenna array through the use of a time-varying control of the antenna array, and to provide at least one system of identifying an effective time variation.

The treatment-planning program may further execute to vary the duration of each power deposition pattern in the treatment schedule to control average power deposition to the tissue region outside the treatment region.

It is thus a feature of at least one embodiment of the invention to better match potential hotspots and suppression regions by control of the relative duration of the antenna settings producing each.

The treatment planning program may further execute to select the order of each power deposition pattern in the treatment schedule according to a thermal model of tissue in the tissue region, the thermal model describing rates of heating and cooling of the tissue in response to changes in applied power.

It is thus a feature of at least one embodiment of the invention to permit control of time-consistency of the hyperthermia treatment.

The treatment-planning program may further accept physician input with respect to a desired minimum temperature in the treatment area and at least one desired maximum temperature in a portion of the tissue region outside of the treatment area.

It is thus a feature of at least one embodiment of the invention to permit sophisticated control of hyperthermia treatments including reduction of temperatures outside of the treatment area in susceptible zones.

The data characterizing the tissue in the tissue region of the patient may characterize the spatial distribution of the electrical properties of the tissue and the model may model microwave propagation throughout the tissue and absorption of microwave power by the tissue.

It is thus a feature of at least one embodiment of the invention to provide a treatment schedule that accurately reflects actual tissue of the patient with respect to microwave transmission.

Alternatively or in addition, the data characterizing the tissue of the tissue structure of the patient may characterize the thermal properties of the tissue and the selection of power deposition patterns may model heating and cooling of the tissue as a function of deposited power and time.

It is thus a feature of at least one embodiment of the invention to accommodate different absorption and thermal dissipation qualities of the actual tissue of the patient.

The selection of power deposition patterns to generate the treatment schedule may iteratively process different power deposition patterns or sequences to maximize an objective function accepting as an argument desired temperature in the treatment region and at least one temperature outside of the treatment region.

It is thus a feature of at least one embodiment of the invention to provide a general mechanism for reducing hotspots inherent in antenna-array focused microwaves.

Each power deposition pattern may be associated with a specific set of amplitude and phases of radiofrequency power for each antenna and may be held constant during a time of the power deposition pattern in the treatment schedule.

It is thus a feature of at least one embodiment of the invention to provide a tractable treatment schedule employing a finite set of time-sequenced antenna settings.

The patient data may be derived from MRI data acquired of the tissue region.

It is thus a feature of at least one embodiment of the invention to provide a source of data that may be matched to accurate thermal and electrical data about the tissue.

A microwave hyperthermia treatment apparatus per the present invention may include an array of antennas positionable about a patient and a radiofrequency power source connected to the antennas to provide radiofrequency power having independently controllable amplitude and phase for each antenna. A treatment controller may be connected to the radiofrequency power source controlling the phase and amplitude of the radiofrequency power for each antenna to change the frequency and amplitude at the antennas over a treatment time according to a treatment schedule, wherein the treatment schedule provides a series of at least three sequentially applied power deposition patterns producing different patterns of heating of tissue of the patient outside of a tumor site.

It is thus a feature of at least one embodiment of the invention to provide a hyperthermia system with improved multi-antenna control by switching between predefined power deposition patterns during the treatment.

The power deposition patterns and associated temperature distribution profiles may provide potential hotspots and suppression regions and the combination of power deposition patterns during the treatment schedule may match hotspots of one power deposition pattern with suppression regions of another power deposition pattern.

It is thus a feature of at least one embodiment of the invention to identify a set of predefined power deposition patterns based on a compensation principle between potential hotspots and suppression regions.

The treatment schedule may be in excess of one second.

It is thus a feature of at least one embodiment of the invention to provide a quasi-static treatment system adaptable to readily available hardware.

The treatment controller may provide discrete switching between the power deposition patterns.

It is thus a feature of at least one embodiment of the invention to permit a simple switch design for implementing the invention.

The radiofrequency power may be between 50 megahertz and 10 gigahertz.

It is thus a feature of at least one embodiment of the invention to provide a system for treatment of tissue within the body and, in particular, the brain.

The treatment schedule may be repeated multiple times in succession during treatment of the patient.

It is thus a feature of at least one embodiment of the invention to permit great flexibility in selecting the power deposition patterns while providing relatively constant treatment temperatures by cycling through a set of predefined power deposition patterns faster than the heating and cooling time of the tissue.

These particular objects and advantages may apply to only some embodiments falling within the claims and thus do not define the scope of the invention.

BRIEF DESCRIPTION OF THE FIGURES

FIG. 5 is a two-dimensional representation of a power deposition pattern describing power applied to the treatment region including hotspots and a corresponding perspective phantom view of the same;

FIG. 6 is a figure similar to that of FIG. 5 showing the identification of suppression regions compensating for the hotspots;

FIG. 7 is a diagrammatic representation of multiple power deposition patterns sequenced together in a treatment schedule;

DETAILED DESCRIPTION OF THE PREFERRED EMBODIMENT

Figure 1:
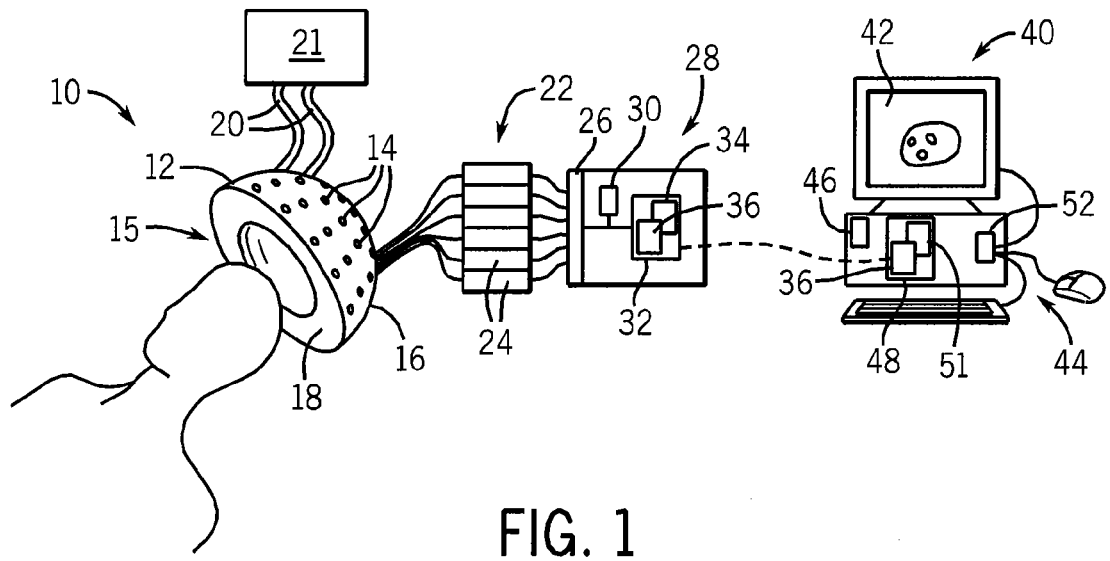
FIG. 1 is a simplified representation of a microwave hyperthermia system for use with the present invention showing an antenna array and a radiofrequency source for controlling phase and amplitude of signals to each antenna under computer control.

Referring now to FIG. 1, a hyperthermia system 10 may provide an antenna fixture 12 supporting a plurality of antennas 14 about a treatment volume 15. In one embodiment, the treatment volume may be defined by a substantially hemispherical shell 16 whose inner surface may contain a collar 18 receiving and supporting the top of the patient's head. The collar may be filled with de-ionized water that may be circulated through connecting hoses 20 with a cooler/pump 21 providing skin cooling of at approximately 15 degrees centigrade of the patient's head to minimize surface heating of the skin by microwave energy from the antennas 14 as will be described.

Figure 2:
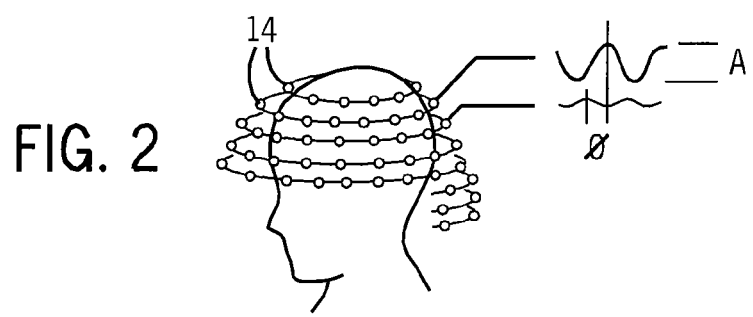
FIG. 2 is a simplified perspective view of the antenna array of FIG. 1 showing the location of antennas about the head and the amplitude and phase of a radiofrequency signal at two example antennas.

Referring also to FIG. 2, the antennas 14 may be arranged at multiple heights along an inferior superior axis of the patient and about an upper portion of the patient's head. The antennas 14 preferably direct microwave energy inward toward the treatment volume 15 and may, for example, be microwave horns or patch antennas or other antennas of a type known in the art and are spaced to provide for substantially uniform separation of less than six centimeters.

In one embodiment, 134 antennas 14 operating at 1 GHz are distributed evenly across five elliptical rings and three partial elliptical rings, each ring separated by two centimeter elevational spacing, the antenna-to-antenna spacing on each ring being approximately four centimeters.

Referring still to FIGS. 1 and 2, each antenna 14 may be connected to a radiofrequency power source 22 providing independent phase (phi) and amplitude (A) control of the radiofrequency power applied to the antenna. The radiofrequency power source 22 may provide a separate radiofrequency amplifier/synthesizer 24 for each antenna 14 or may use a single radiofrequency power source with separate amplitude and phase shifters. In one embodiment, a set of discrete phases and amplitudes may be implemented in a switching fashion.

The radiofrequency power source 22 may be controlled by a treatment controller 28 via an interface board 26, for example, providing a multiplexed A/D converter outputting phase and amplitude values from the treatment controller 28. The treatment controller 28 may include a processor 30 communicating with a memory 32 holding a stored program 34 and treatment plan data 36 describing a treatment schedule of changing phases and amplitudes of microwave frequency to be applied to the antennas 14 during treatment.

The treatment plan data 36 may be developed on the treatment controller 28 but preferably is developed off-line on a separate workstation 40 having a display 42 for displaying treatment maps for physician input, as will be described, generated by a communicating standard desktop computer 44 also having a processor 46, a stored memory 48 holding a treatment planning program 51 and the treatment plan data 36, the latter which may be transferred to treatment controller 28. The desktop computer 44 may also communicate with input devices 50 by interface 52 according to well understood techniques for physician input as will be described. It will be appreciated that the processing and data storage required by the present invention may be freely distributed among one or more processors and different types of computers according to well-understood techniques.

Figure 3:
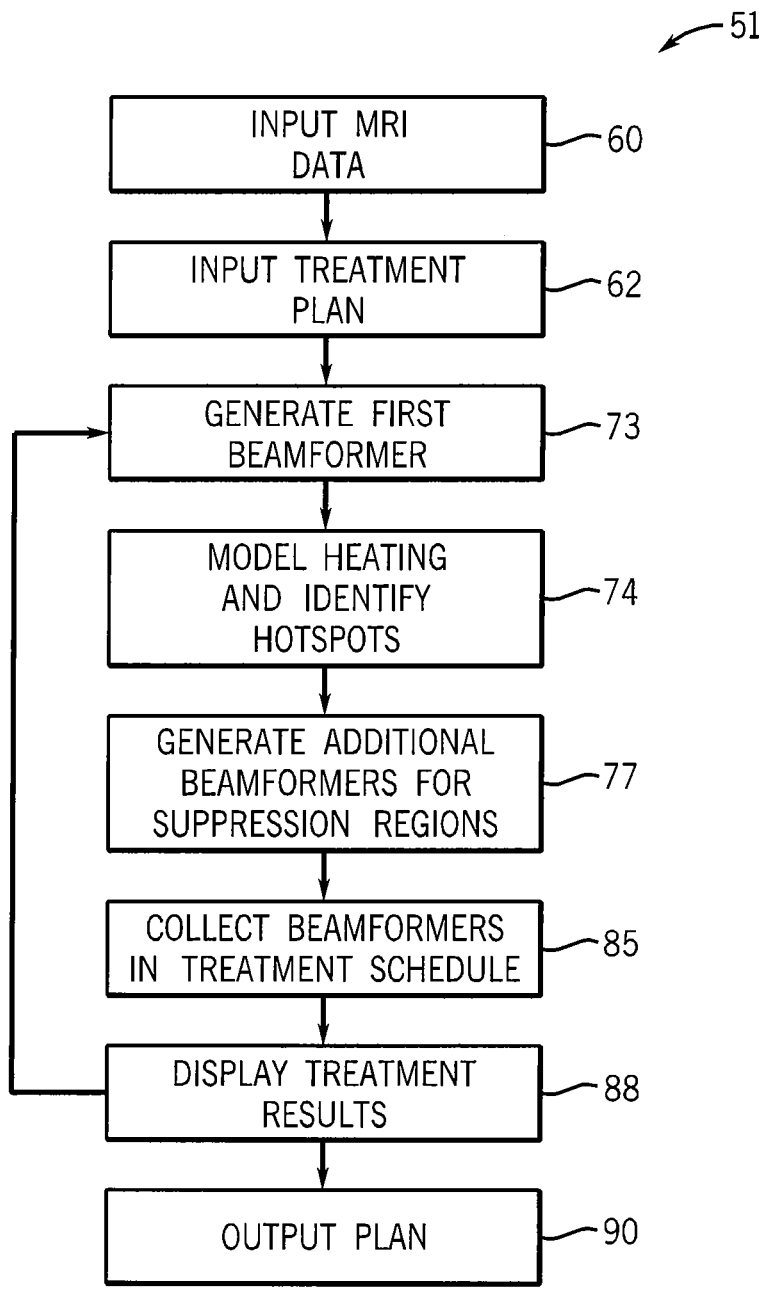
FIG. 3 is a flow chart of the present invention describing the steps of developing a treatment schedule for controlling the antenna array of FIG. 2.

Referring now to FIG. 3, in developing treatment plan data 36, the treatment planning program 51 may first receive MRI input data, as indicated by process block 60, of the particular patient to be treated. The treatment plan data may be registered to fiducial points such as bony prominences of the patient's skull or points on a stabilization fixture also alignable with the fixture 12. This MRI data may be displayed on the display 42 for reference by a physician for development of a treatment map, to be described, and is preferably applied to a stored encyclopedia of tissue types to identify thermal and electrical characteristics of the tissue in different regions of the patient's brain.

Figure 4:
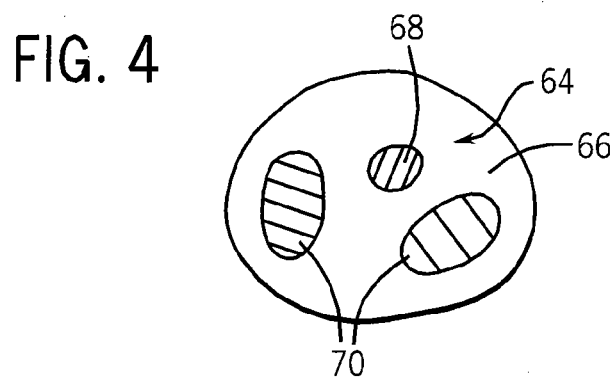
FIG. 4 is a treatment map as may be defined by a physician for a particular treatment.

At process block 62, the treatment map 64 is prepared using the workstation 40, for example, by displaying successive slices of a tissue region 66 of the patient as shown in FIG. 4 which together describe volumetric data encompassing a tissue subject to microwave exposure. The slices may be reviewed by the physician to define a treatment region 68 within the tissue region 66 where elevated temperatures are desired for hyperthermia treatment. The boundaries of the treatment region 68 and desired minimum temperatures in one or more zones of this treatment region 68 may be entered by the physician or automatically set.

Optionally, the physician may also define one or more protection regions 72 to which maximum desired temperatures or other temperature constraints, such as measures of uniformity or the like, may be applied. Generally, the tissue region 66 outside the treatment region 68 will be limited to a temperature of 41 degree centigrade or less.

At process block 73, the treatment-planning program 51 generates an initial "beamformer" being a set of independent amplitude and phases of microwave electromagnetic radiation to be applied to each of the antennas 14. This initial beamformer is selected to maximize the fraction of deposited power density in the treatment region 68 with respect to the deposited power density outside the treatment region 68, although other similar constraints may be used that promote a focusing of power deposition in the treatment region 68. This beamformer may be generated, for example, by treating a set of linear equations providing phase and amplitude values for each antenna and incorporating microwave propagation characteristics of the patient tissue derived from the MRI data of process block 60 between each antenna and each voxel of tissue in the tissue region 66.

Referring to FIGS. 3 and 5, at process block 74 tissue temperatures generated by the initial beamformer are then modeled using the thermal and electrical characteristics of the tissue of the patient to provide a power deposition pattern 76 (depicted two-dimensionally but preferably three-dimensional) that shows deposited power or tissue temperature at different portions of the tissue region 66 for predetermined duration of treatment, for example, the time required to raise the temperature within the treatment region 68 to 43-44 degrees centigrade. Typically, this power deposition pattern 76 will also show one or more hotspots 78a-c being areas of elevated power deposition or temperature outside of the treatment region 68. For example, hotspots 78 may be defined as voxels in the head but outside of the treatment region 68 whose temperature exceeds 41 degrees centigrade or voxels exceeding a temperature of a susceptible region defined by the physician.

Referring now to FIGS. 3 and 6, at succeeding process block 77, a suppression region 80 may be defined around each hotspot 78. In one embodiment, for convenience, these suppression regions 80 are defined as spheres of approximately ten percent of the brain volume. Each suppression region 80 may be centered on a peak temperature of each hotspot 78. For hotspots 78 larger than a suppression region 80, such as hotspot 78a as depicted, an iterative process may be used where a first suppression region 80a is centered on a peak temperature of the hotspot 78a and then subsequent suppression regions 80b and 80c are applied to portions of the hotspot 78a not already circumscribed by a suppression region 80a centered on a peak temperature of those remaining regions, and so forth until all hotspots 78 are completely covered.

Referring now to FIG. 7, additional beamformers 84 are then generated, each defining the phase and amplitude of power at a respective antenna 14 using a process similar to that described with respect to process block 73 but with an optimization that maximizes power to the treatment region 68 and limits power to the suppression regions 80. For example, the fraction described above with respect to the initial beamformer may be used with additional weighting provided to the desired suppression regions 80 of the tissue regions 66 outside of the treatment region 68.

In one embodiment, different beamformers 84 may be generated each preserving a different suppression region 80 associated with each of the suppression regions identified in process block 77 to produce a number of beamformers 84 equal to the number of desired suppression regions 80. In addition, one beamformers 84 may be developed providing suppression of power in the union or combinations of all suppression regions 80, and one beamformer 84 may be developed without consideration of any of the suppression region 80 to emphasize treatment of the treatment region 68. In a general case, some of these beamformers 84 preserving suppression regions 80 will generate power deposition patterns 76 having additional hotspots 78'. Typically these hotspots 78' will be in different locations than the hotspots 78 of the initial beamformer. More typically, however, beamformers 84 emphasizing suppression regions 80 will have no new hotspots 78 or minor hotspots 78 beyond those identified at process block 74.

Referring now to FIGS. 3 and 7, at process block 85, the beamformers 84 may be arranged in order and given durations to create a treatment schedule 86 that will be used to control the antennas 14 during treatment of the patient. Typically the treatment schedule 86 will have a duration of greater than one second to permit simplified control of the radio frequency amplifier but shorter than a thermal time constant of the tissue. In one embodiment, the treatment schedule 86 may be cycled periodically for multiple times to provide the desired length of treatment but also to provide rapid switching among beamformers 84 for more consistent temperature generation.

The process of ordering and determining the length of time for each beamformer 84 in the treatment schedule 86 takes into account the thermal model of the tissue with respect to its cooling and heating under the application of power. This treatment schedule 86 may be determined automatically by an optimization process such as linear programming according to a goal of maximizing a uniformity of the heating of the tissue region 66 outside of the treatment region 68 or minimizing an error (for example, the least squared error) between the average temperature outside the treatment region 68 and the desired treatment map 64. The determination of the treatment schedule 86 may also take into account the historical thermal state of the tissue implicit in the ordering to promote time uniformity in the produced temperatures, something that is also promoted by short time slices.

Figure 8:
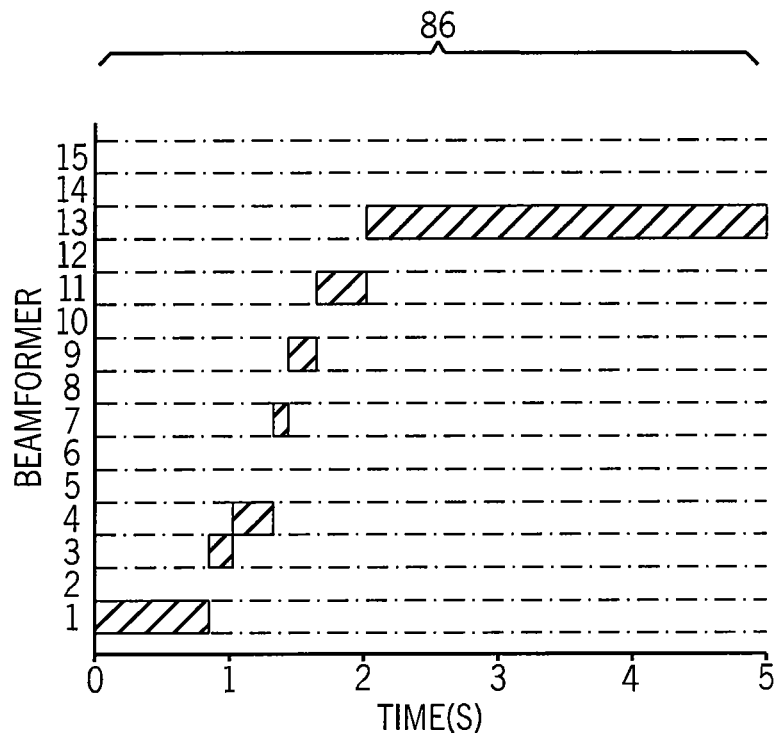
FIG. 8 is a graph showing example durations of the application of each power deposition pattern.

Referring now to FIG. 8, an example treatment schedule 86 will cycle through different beamformers 84 (indicated on the vertical axis) for different periods of time (indicated on the horizontal axis) according to this optimization. In this example, beamformer number 13 was optimized to cover all of the suppression regions 80 and accounts for more than half the duration of the treatment schedule 86. Notably, some beamformers 84 are not used or given zero weighting.

Once the sequence of the treatment schedule 86 is complete, the treatment schedule 86 may be modeled and the resulting temperature distributions and other treatment statistics (e.g. maximum temperatures and durations) reviewed by the physician as indicated by process block 88. If the treatment schedule 86 is approved, the treatment plan may be output as the treatment plan data 36 of FIG. 1 as indicated by process block 94 to provide real-time control of the hyperthermia system 10.

Referring again to FIG. 3, it will be recognized that at process block 88, the process of process blocks 73, 74, 77, 85, and 88 may be repeated, for example, with a different initial beamformer 84 at process block 73 or different linear programming criteria or the like to provide for an iterative process or alternative solutions meeting different goals. Alternatively, or in addition, this iteration may be used in a more general global optimization approach described below.

Figure 9:
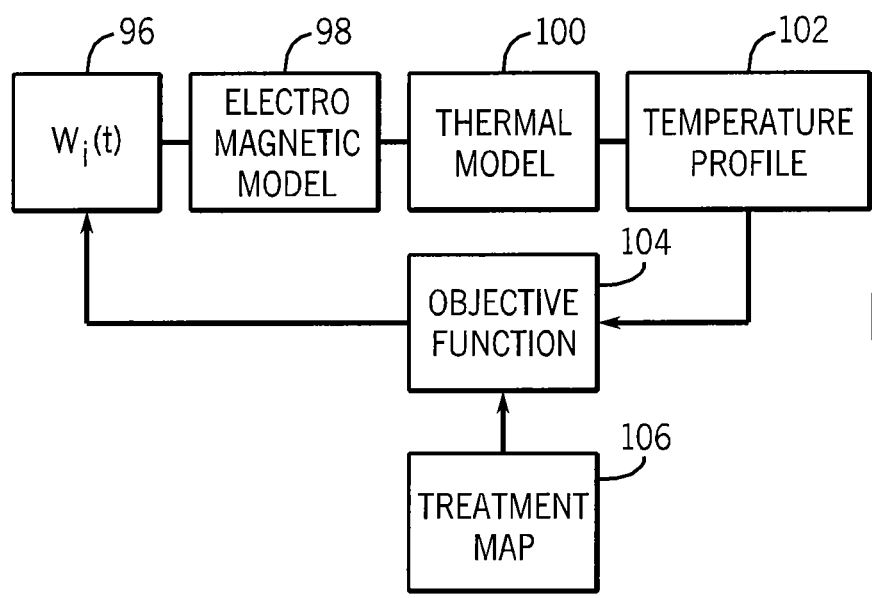
FIG. 9 is a block diagram of a general iterative optimization system that may be used with the present invention.

Referring now to FIG. 9, while the present invention has provided one method of choosing and ordering multiple beamformers 84, using an initial definition of a beamformer and a matching of hotspots 78 to suppression regions 80, it will be appreciated that other mathematical techniques may also be used for this purpose of creating an evolving sequence of beamformers. Such techniques include general global optimization techniques including stochastic optimization methods such as simulated annealing and the like. Generally each of these concepts will provide an initial seed set 96 of phases and amplitudes $W_i$ for the antennas 14 for different times (t) and will apply them to an electromagnetic model of the tissue 98 and a thermal model of the tissue 100 to provide for a modeled temperature profile 102. This temperature profile may be analyzed by an objective function 104 (for example considering any or all of peak temperature values, tissue damage, treatment speed, uniformity, accuracy and the like) typically incorporating input information 106 provided by the physician indicating desired treatment zones temperatures and metrics. The output of the objective function is used to modify the seed set 96 and its time sequence until the desired optimization is produced as measured by a threshold applied to the output of the objective function 104.

Importantly, the present invention produces not a single set of phases and amplitudes but a schedule of different phases and amplitudes reflecting the fact that a single such set of phases and amplitudes necessarily results in the creation of limiting hotspots. While the application of the beamformers per FIG. 8 is shown in discrete steps, it will be appreciated that the transitions in phase and amplitude may implemented as smooth transitions between states if desired. Nevertheless, the present invention anticipates a finite number of calculated beamformers.

It will further be appreciated that the invention is not limited to antenna arrays but that other means for producing spatially directive patterns, such as microwave lenses may be used. In addition, the invention may employ a spatially scanning (e.g., mechanically moved) set of antennas may be used to provide a time-varying spatial pattern of energy providing an effective antenna array of multiple emitters. That is, the set of microwave emitters may be implemented by as few as one emitter moved between locations and provided different amplitudes and phases of microwave power.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A microwave hyperthermia treatment system comprising:
    a set of microwave emitters positionable about a patient;
    a radiofrequency power source connected to the microwave emitters to provide radiofrequency power having independently controllable amplitude and phase for each microwave emitter; and
    a treatment controller connected to the radiofrequency power source controlling the phase and amplitude of the radiofrequency power for each microwave emitter to change the frequency and amplitude at the microwave emitters over a treatment time according to a treatment schedule determined and stored in non-transitory medium before application of power to the microwave emitters for treatment of the patient and executed by the treatment controller during application of power to the microwave emitters for treatment of the patient, wherein the treatment schedule provides a predetermined series of at least three sequentially applied power deposition patterns producing different patterns of heating of tissue of the patient within and outside of a tumor site so that radiofrequency power is concentrated within the tumor site; and wherein the power deposition patterns each provide different hotspots and suppression regions and wherein the treatment schedule matches predetermined hotspots of one power deposition pattern with predetermined suppression regions of another power deposition pattern to control and differentiate an average power deposition in the tissue region inside and outside the treatment region.

2. The microwave hyperthermia treatment system of claim 1 wherein the treatment schedule is in excess of one second.

3. The microwave hyperthermia treatment system of claim 1 wherein the treatment controller provides discrete switching between the power deposition patterns.

4. The microwave hyperthermia treatment system of claim 1 wherein the radiofrequency power is between 500 megahertz and two gigahertz.

5. The microwave hyperthermia treatment system of claim 1 wherein the microwave emitters are positioned to proximately encircle a human head at different elevations on an inferior/superior axis.

6. The microwave hyperthermia treatment system of claim 1 further including a skin cooling mechanism within a fixture holding the set of microwave emitters at predetermined locations with respect to the patient.

7. The microwave hyperthermia treatment system of claim 1 wherein the treatment controller includes a computer executing a stored program to:
   (a) receive data characterizing tissue in a tissue region of a patient;
   (b) receive data defining a treatment region being a portion of the tissue region;
   (c) generate a set of power deposition patterns for the set of microwave emitters, where for each power deposition pattern the microwave emitters have different given amplitudes and phases of radiofrequency power;
   (d) iteratively select among the power deposition patterns to generate a treatment schedule of a series of power deposition patterns which when applied to the tissue region of the patient provide an elevated heating of the treatment region and reduced heating of the tissue region outside the treatment region within predefined limits.

* * * * *